US00PP16114P3

(12) United States Plant Patent
Eremin

(10) Patent No.: US PP16,114 P3
(45) Date of Patent: Nov. 15, 2005

(54) *PRUNUS* PLANT NAMED 'LC-52'

(50) Latin Name: ***Prunus Cerasus*×*(P. Cerasus*×*P. Maaki)***
Varietal Denomination: LC-52

(75) Inventor: Guennadi Eremin, Krymsk (RU)

(73) Assignee: Varieties International, LLC, Dundee, OR (US)

( * ) Notice: Subject to any disclaimer, the term of this patent is extended or adjusted under 35 U.S.C. 154(b) by 450 days.

(21) Appl. No.: 09/880,950

(22) Filed: Jan. 11, 2002

(65) Prior Publication Data

US 2004/0034892 P1 Feb. 19, 2004

(51) Int. Cl.[7] ..... A01H 5/00

(52) U.S. Cl. ..... Plt./183

(58) Field of Search ..... Plt./183

*Primary Examiner*—Anne Marie Grunberg
*Assistant Examiner*—W. C. Haas
(74) *Attorney, Agent, or Firm*—The Webb Law Firm

(57) ABSTRACT

A new and distinct rootstock variety of *Prunus* named 'LC-52' that is characterized by, the ability to serve well as rootstock that is compatible with all other cherries, wide leaves, semi-dwarf habit and hardiness to −15° Centigrade. In combination these traits set the new cultivar apart from all other existing varieties of *Prunus* rootstock.

1 Drawing Sheet

Botanical classification: *Prunus Cerasus*× (*P. Cerasus*×*P. Maaki*).
Varietal denomination: 'LC-52'.

CROSS REFERENCE TO RELATED APPLICATIONS

The application for the new invention *Prunus* Plant Named 'LC-52' will be co-pending with three other applications entitled *Prunus* Plant Named 'VVA-1', Ser. No. 09/880,962, *Prunus* Plant named 'VSL-2', Ser. No. 09/880,953, and *Prunus* Plant Named 'VSV-1', Ser. No. 09/880,951 having the same filing date and inventor.

BACKGROUND OF THE INVENTION

The present invention relates to the new and distinct cultivar known botanically as a hybrid of *Prunus* and referred to hereinafter as 'LC-52'. The new invention was bred by the inventor in a cultivated area. It is a hybrid that resulted from a breeding program at the Breeding Station in Krymsk, Russia.

The breeding program, at the Breeding Station, was established in 1964 and funded by the government of the former Soviet Union for the purpose of producing new and improved *Prunus* cultivars that serve well as rootstock that is compatible with all other cherries, and that propagate well using softwood cuttings and meristem cuttings in vitro.

In 1964 the inventor crossed the female *Prunus cerasus* (not patented) with the male hybrid (*Prunus cerasus*×*Prunus maakii*) (not patented) producing an induced hybridization in a cultivated area of Krymsk, Russia. The resulting seedlings were planted at the Breeding Station where they were observed and evaluated for ten years. In 1974 the inventor selected 'LC-52' from these seedlings. The new cultivar originated as a single plant and is the result of a hybrid cross between *Prunus cerasus* (not patented) and (*Prunus cerasus*×*Prunus maakii*) (not patented).

The closest comparison plants are the parent plants. The characteristics that distinguish the new cultivar from the female parent are, smaller fruit, bitter fruit and ease of propagation. The new cultivar differs from the male parent by exhibiting wider leaves, larger fruit and smaller overall size. 'LC-52' is unique from all other existing varieties of *Prunus* in its ability to serve well as rootstock that is compatible with all other cherries and its ability to remain hardy to −15° Centigrade.

'LC-52' was first asexually propagated in 1974 by the inventor at the Breeding Station in Krymsk, Russia. The method used was softwood cuttings. The distinguishing traits have been determined stable and are reproduced true to type in successive generations.

SUMMARY OF THE INVENTION

The following traits have been repeatedly observed and represent the characteristics of the new cultivar. These traits in combination distinguish 'LC-52' from all other existing varieties of *Prunus* known to the inventor. 'LC-52' has not been tested under all possible conditions and phenotypic differences may be observed with variations in environmental, climatic, and cultural conditions, however, without any variance in genotype.

1. 'LC-52' serves well as rootstock that is compatible with all other cherries.
2. 'LC-52' propagates well by softwood cuttings and meristem cuttings in vitro.
3. 'LC-52' exhibits wide leaves.
4. 'LC-52' exhibits a dwarf habit.
5. 'LC-52' is hardy to −15° Centigrade.

DESCRIPTION OF THE DRAWING

The accompanying photographic drawing illustrates the new cultivar, with the color being as nearly true as possible with color illustrations of this type. The drawing shows a tree of the new variety.

BOTANICAL DESCRIPTION OF THE PLANT

The following is a detailed botanical description of the new rootstock variety *Prunus* 'LC-52'. Observations, measurements, values, and comparisons were collected in McMinnville, Oreg. from the inventor. The new variety was from three years old when described and was cultivated in a temperature variable environment having warm summers and cold winters. The foliage, flower and fruit exhibited by this cultivar are of no economic or commercial value, therefore comparisons and botanical descriptions of the foliage, fruit and flower are made for identification purposes only. Mature specimens, as well as bareroot specimens, were unavailable for photographing at the time this document was written. The color determinations are in accordance with The R.H.S. Colour Chart of The Royal Horticultural Society, London England except where general color terms of ordinary dictionary significance are used.

Botanical classification: *Prunus Cerasus*×(*P. Cerasus*×*P. Maaki*).

Parentage: *Prunus* 'LC-52' is an induced hybrid that resulted from crossing the following plants.

*Female parent.*—*Prunus cerasus* (not patented).

*Male parent.*—(*Prunus cerasus*×*Prunus maakii*) (not patented).

Type: Deciduous tree.

Use: *Prunus* 'LC-52' serves well as rootstock for all other cherries.

Soil: All types of soil.

Light: Full sunlight.

Fruit bearing: The new variety is a rootstock to induce the precocity of a cherry tree; it induces production of fruit approximately 1 to 2 years earlier of the grafted plants.

Crop time: 4 years is required for a rooted cutting to achieve finished product size that is ready to ship bareroot to use as rootstock.

Dimensions at crop time: 3.5 m in height and 3 m. in width at 4 years.

Vigor: 60–70% of standard using *Prunus avium* as standard (sweet cherry seedling).

Habit: Semi-dwarf and erect.

Hardiness: USDA Zone 5A.

Cold tolerance: Relatively hardy, more so than *Prunus avium.*

Heat tolerance: Excellent; the new variety withstands temperatures over 100° F.

Propagation: Propagated by softwood cuttings and meristem cuttings in vitro.

Rooting habit: Fine and fibrous initially. After 1 year the roots become fleshy and thick.

Time to initiate roots: 6 months are required to develop roots at 22–25° Centigrade, for both softwood cuttings and meristem cuttings in vitro.

Disease and insect resistance: Normal resistance to disease and insects.

Trunk:

*Trunk dimensions.*—6 cm. in diameter at 20 cm in height above soil at 4 years.

*Trunk bark surface.*—Glabrous surface.

*Trunk bark color.*—178A.

*Lenticels.*—Present in moderate amounts; the exact number is not ascertainable.

*Lenticel dimensions on trunk.*—2–3 mm. in length and 1 mm. in width.

*Lenticel color.*—198B.

*Lenticel shape.*—Ovoid.

Branches:

*Branch surface.*—Glabrous surface.

*Branch color.*—175A.

*Internode length.*—5–10 cm. between nodes.

*Branching angle at emergence.*—60° angle.

*Branching habit.*—Freely branching with many branches.

*Pubescence.*—Absent.

*Branch lenticels.*—Present in moderate amounts; the exact number is not ascertainable.

*Lenticel shape.*—Lens shaped.

*Lenticel color.*—198B.

*Lenticel dimensions.*—2 mm. in length and 1 mm. in width on the branches.

Leaves:

*Arrangement.*—Alternate and whorled.

*Leaf length.*—4–4.5 cm. in length.

*Leaf width.*—3–3.5 cm. in width.

*Leaf shape.*—Oval.

*Leaf apex.*—Acuminate.

*Leaf base.*—Rounded.

*Leaf color* (*adaxial surface*).—139B.

*Leaf color* (*abaxial surface*).—139C.

*Leaf surface* (*adaxial*).—Glabrous surface.

*Leaf surface* (*abaxial*).—Glabrous surface.

*Leaf margins.*—Crenulate.

*Leaf division.*—Simple.

*Petiole dimensions.*—0.80–1 cm. in length and 1 mm. in width.

*Petiole color.*—149C.

*Petiole surface.*—Glabrous.

*Leaf stipules.*—Absent.

*Leaf pubescence.*—Absent.

*Venation pattern.*—Pinnate.

*Vein color* (*adaxial and abaxial surfaces*).—141B.

*Leaf texture.*—Glabrous texture.

*Leaf strength.*—Moderate strength.

*Leaf appearance.*—Glossy with young leaves involuted.

Fruit:

*Maturity.*—Requires 70–72 days to mature.

*Dates of picking.*—Not a fruit crop. Fruit has no commercial value. Because the new variety is used as a rootstock, the growers do not typically allow the new variety to bear fruit.

*Production.*—Low. Produces a small amount of fruit.

*Fruit form.*—Globose.

*Stem dimensions.*—2–2.5 cm. in length and 1 mm. in width.

*Stem color.*—144A.

*Skin color.*—187A.

*Skin surface.*—Glabrous surface.

*Lenticels.*—Absent on fruit.

*Flesh color.*—187C.

*Flesh texture.*—Juicy texture.

*Flavor.*—Bitter cherry flavor.

*Aroma.*—None.

*Seed number.*—One drupe.

*Seed shape.*—Round shape.

*Seed color.*—164B.

*Seed dimensions.*—2–2.5 mm. in diameter and 2–2.5 mm. in length.

*Storage.*—Not determined because fruit has no commercial value.

*Use.*—Fruit is not recommended for consumption and has no commercial value.

Flower:

*Arrangement.*—Solitary.
*Flower shape.*—Rotate.
*Bud dimensions.*—3 mm. in width and 3 mm. in length.
*Bud color.*—155C.
*Time of bloom.*—Flowers bloom when the plant is 2 years old and the flowers last for 7–8 days.
*Flower diameter.*—2.5–3 cm. in diameter.
*Flower depth* (*throat*).—2–2.5 mm. in depth.
*Bloom quantity.*—50–60 flowers per branch.
*Number of petals.*—Five petals in number.
*Fused or unfused.*—Petals are unfused.
*Petal shape.*—Oval.
*Petal margin.*—Entire and slightly wavy.
*Flower color fully opened* (*upper and lower surfaces*).—155C.
*Dimensions of peduncle.*—2–2.2 cm. in length and up to 1 mm. in width.
*Color of preduncle.*—144B.
*Surface of peduncle.*—Glabrous.
*Calyx dimensions.*—2 mm. in length and 4 mm. in width.
*Calyx surface.*—Glabrous surface.
*Pubescence.*—Absent.
*Calyx color.*—152C.
*Number of sepals.*—Five sepals in number.
*Natural flowering season.*—Spring.
*Persistent or self-cleaning.*—Self-cleaning.
*Fragrance.*—None.

Reproductive organs:

*Stamen number.*—Polyandrous. 20–25 stamens and unequal length.
*Stamen color.*—145C.
*Anther shape.*—Round with stamen attached at center of dorsal surface.
*Anther color.*—9A.
*Anther dimensions.*—1 mm. in length and 1 mm. in width.
*Amount of pollen.*—Large amount of pollen.
*Color of pollen.*—9A.
*Pistil.*—One in number.
*Pistil color.*—144C.
*Pistil dimensions.*—1.2 cm. in length and 1 mm. in width.
*Style color.*—144C.
*Style form.*—Elongate.
*Style dimensions.*—1 mm. in length and 1 mm. width.
*Ovary dimensions.*—2 mm. in length and 2 mm. in width.
*Ovary color.*—155C.
*Ovary position.*—Superior.

It is claimed:

1. A new and distinct variety of *Prunus* plant named 'LC-52' as herein described and illustrated.

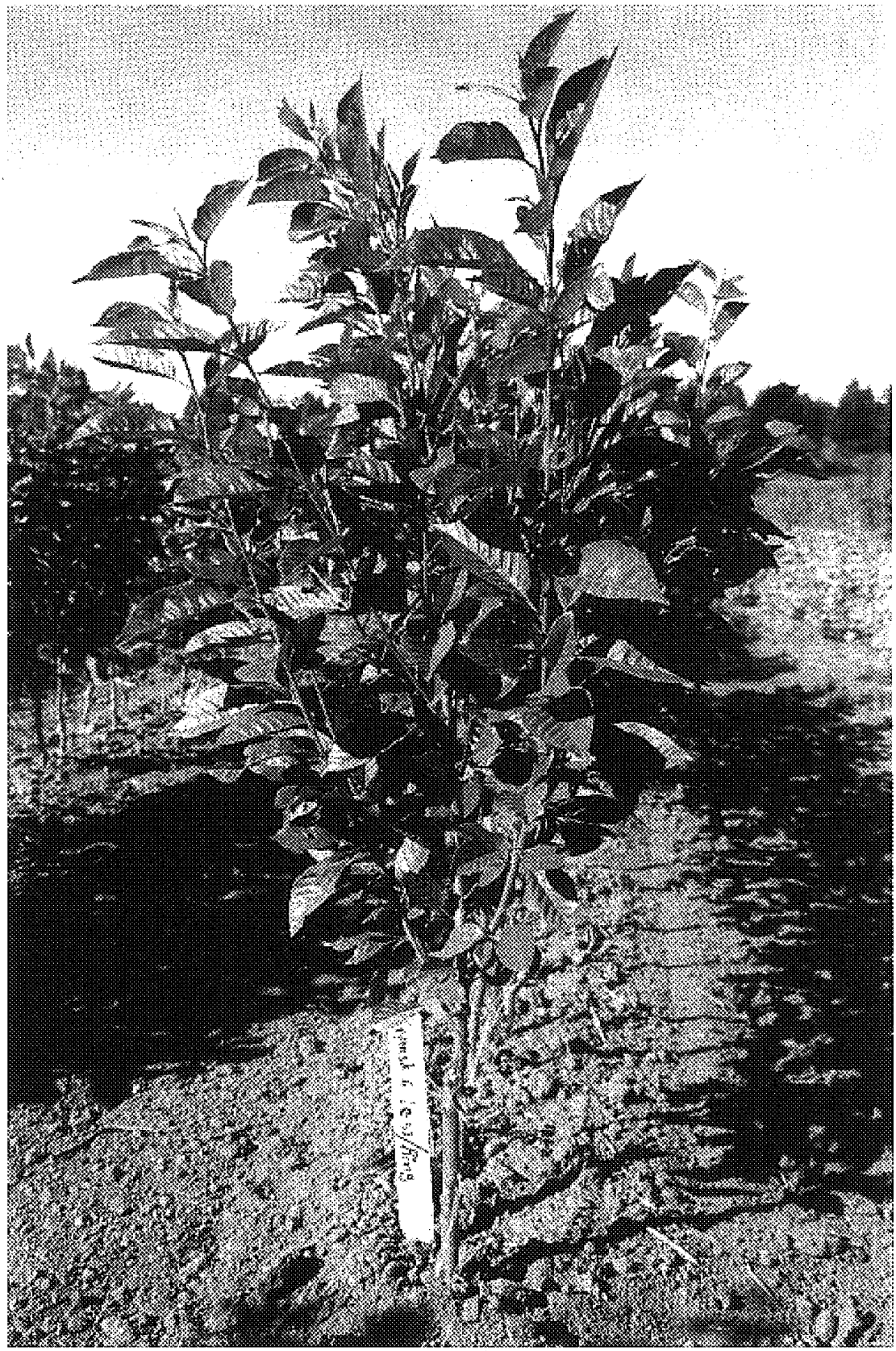

* * * * *